United States Patent [19]

McLachlan et al.

[11] Patent Number: 5,303,036
[45] Date of Patent: Apr. 12, 1994

[54] VARIABLE PATH LENGTH LIGHT TRANSMISSION PROBE

[75] Inventors: Richard D. McLachlan; Mary A. Leugers; Robert A. Bredeweg, all of Midland, Mich.

[73] Assignee: The Dow Chemical Company, Midland, Mich.

[21] Appl. No.: 765,756

[22] Filed: Sep. 26, 1991

[51] Int. Cl.⁵ .................. G01N 21/00; G01N 21/15
[52] U.S. Cl. .................. 356/440; 356/436; 359/838
[58] Field of Search .............. 356/413, 414, 417, 432, 356/436, 440, 73, 448; 359/883, 884, 721, 731, 638, 636, 629, 871, 838; 250/573-576

[56] References Cited

U.S. PATENT DOCUMENTS

| | | |
|---|---|---|
| 2,647,441 | 8/1953 | Boydston et al. ............... 359/884 |
| 3,164,663 | 1/1965 | Gale . | 
| 3,544,224 | 12/1970 | Friedl . |
| 3,663,109 | 5/1972 | Sharples . |
| 4,081,807 | 3/1978 | Urano et al. ............... 359/636 |
| 4,579,457 | 4/1986 | Guigues ............... 356/436 |
| 4,637,729 | 1/1987 | Schoch ............... 356/410 |
| 4,678,326 | 7/1987 | Harjunmaa ............... 356/417 |
| 4,753,530 | 6/1988 | Knight et al. ............... 356/73 |
| 4,786,171 | 11/1988 | LeFebre et al. ............... 356/413 |

Primary Examiner—Vincent P. McGraw
Assistant Examiner—K. P. Hantis
Attorney, Agent, or Firm—John K. McCulloch; Timothy S. Stevens

[57] ABSTRACT

A probe for use in situ analysis of light absorbing fluids wherein light emitted from a source is collimated by a lens and transmitted through a fluid onto and substantially perpendicular to a reflector. Light is reflected by the reflector back through the fluid and focused by the lens onto a reflected light collector for transmission to analyzing apparatus. The length of the path traversed by the emitted and reflected light is adjustable.

1 Claim, 2 Drawing Sheets

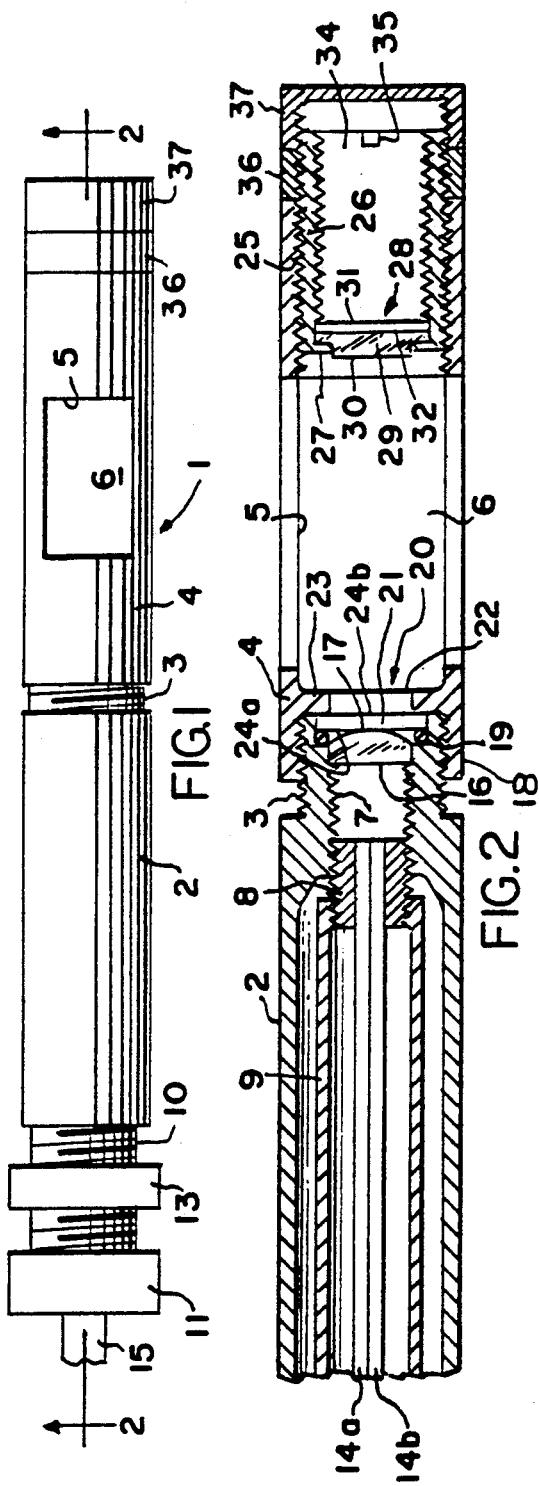
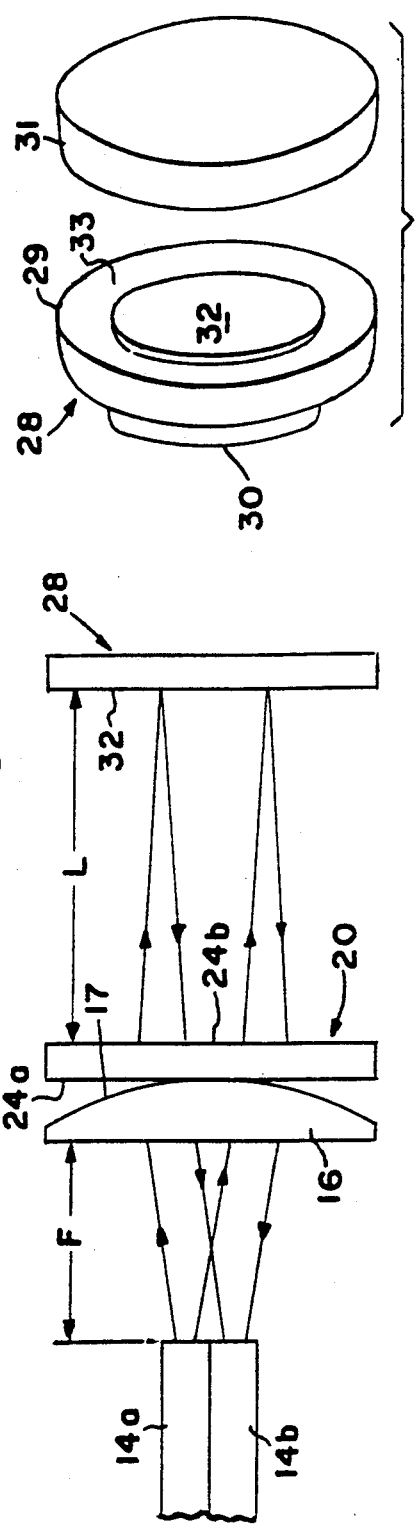
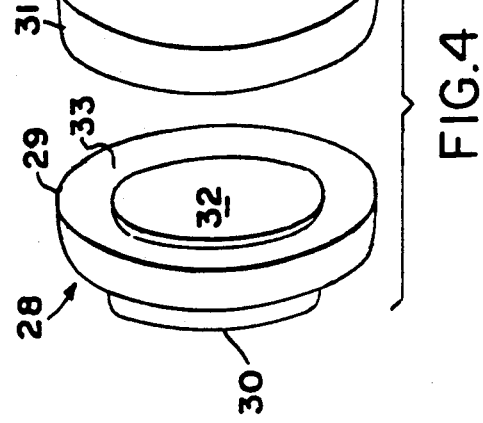
FIG. 1
FIG. 2
FIG. 3
FIG. 4

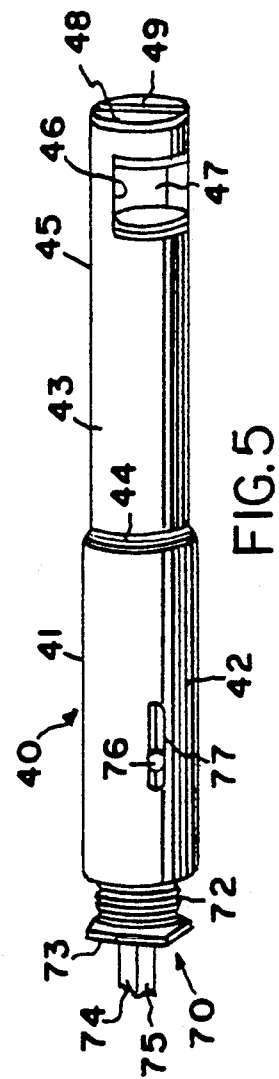
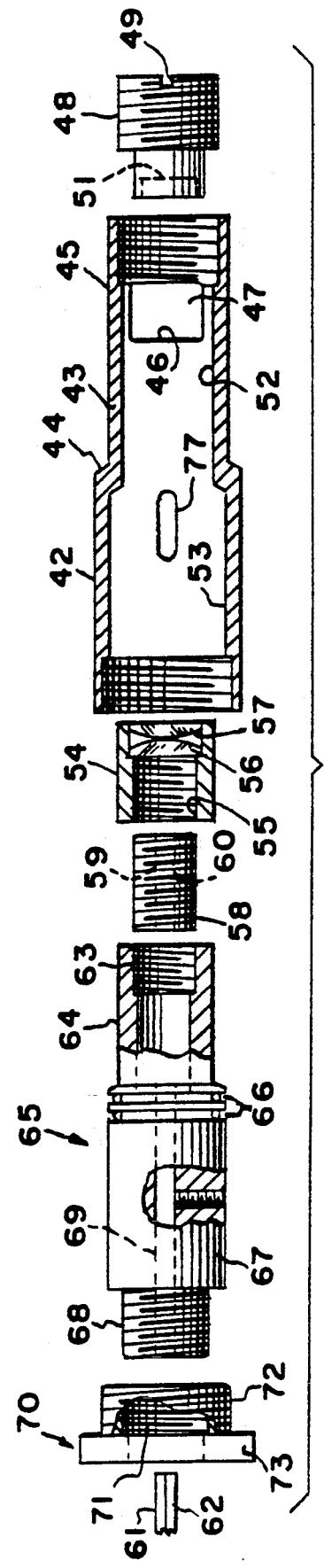

VARIABLE PATH LENGTH LIGHT TRANSMISSION PROBE

This invention relates to a light transmission probe for use in measuring in situ the absorbance of light by fluid media.

BACKGROUND OF THE INVENTION

It is common practice in the analysis of light absorbing fluids to immerse in the fluid one end of a probe having an opening therein through which the fluid may flow, transmit light from a source across the opening onto a reflector which reflects the light back across the opening, collect the reflected light, and conduct it to one or more devices for analysis.

There are many occasions in which it would be desirable to adjust the length of the path across the opening. For example, the translucency of one fluid may be sufficient to enable light to traverse a relatively short path, but insufficient to enable the light to traverse a longer path. By adjusting the length of the light path variations in translucency can be accommodated.

Heretofore, adjustment of the length of the light path has been accomplished by removing one mirror support and substituting therefor another mirror support which, when installed in the probe, provides a different path length to be traversed by the illuminating light and the reflected light. This kind of adjustment is troublesome and time consuming inasmuch as it necessitates physical replacement of one mirror support with another.

Light transmitted by conventional probes often is introduced into the fluid medium in such manner that the light is refracted in its passages through the fluid, thereby making it difficult, if not impossible, to analyze simultaneously light of different wave lengths.

Conventional probes of the general class to which the invention relates utilize reflectors exposed to the fluid with which they are used, thereby subjecting the reflective surfaces thereof to damage, either as a result of handling or from contact with the fluid in which the probe is immersed.

Apparatus constructed in accordance with the invention overcomes the objectionable characteristics referred to above of known probes for the in situ analysis of light absorbing fluids.

SUMMARY OF THE INVENTION

A probe constructed in accordance with the invention comprises an elongate body having between its ends an opening through which a fluid to be analyzed may flow. Light from a source is transmitted longitudinally of the body via an illuminating optical fiber, collimated by a lens, and directed through a transparent window across the opening and through the fluid onto a planar mirror or other reflective surface. Light reflected by the mirror retraverses the opening and the fluid and impinges upon the lens which focuses the reflected light onto another optical fiber which collects the light and conducts to it analyzing apparatus. The illuminating and collecting fibers are located at the focal length of the collimating lens.

The reflective surface preferably is provided by a reflective coating applied to that surface of a transparent body which is remote from the opening and does not come into contact with the fluid. The reflective coating may be sandwiched between the transparent body and a backing member that are secured to one another by a suitable epoxy or other adhesive which not only bonds the two members to one another, but also seals the reflective coating against the possibility of damage either by handling or contact with the fluid.

A transparent window is interposed between the collimating lens and the reflector to protect the lens and the optical fibers from the fluid in which the probe is immersed.

The length of the pat traversed by the light between the window and the reflective surface is adjustable. According to one embodiment of the invention the adjustment may be effected by movement of the reflector toward or away from the window. In another embodiment the position of the reflector is fixed and the adjustment of the path is effected by movement of the assembly of the fibers, lens, and window toward or away from the reflector.

THE DRAWINGS

Apparatus constructed in accordance with two preferred embodiments of the invention is illustrated in the accompanying drawing, wherein:

FIG. 1 is a fragmentary, elevational view of one embodiment of the probe;

FIG. 2 is an enlarged, sectional view taken generally on the line 2—2 of FIG. 1;

FIG. 3 is an enlarged, diagrammatic view of portions of the apparatus;

FIG. 4 is an enlarged, exploded, isometric view of a reflector;

FIG. 5 is an assembled, isometric view of a second embodiment of the probe; and

FIG. 6 is an exploded sectional view of the second embodiment of the probe.

DETAILED DESCRIPTION

A probe constructed in accordance with the embodiment of the invention shown in FIGS. 1-4 is designated generally by the reference character 1 and comprises a tubular body member 2 terminating at one end in a threaded extension 3. The extension 3 is threadedly accommodated in one end of a sleeve 4 having a pair of diametrically opposed openings 5 therein forming a transverse passage 6 through which a fluid medium may flow.

That end of the body 2 adjacent the extension 3 is provided with a reduced diameter, internally threaded portion 7 in which is threadedly accommodated one end of an optical fiber support 8, the opposite end of which is threaded into and fixed in one end of a tube 9 which extends rearwardly beyond the body 2. A longitudinally extending, externally threaded bushing 10 is threadedly fitted into the rear end of the body 2 and provides a slideable support for the tube 9. The bushing carries a conventional fitting 11, such as a Swagelock coupling and a lock nut 13 by means of which the tube 9 is secured in place longitudinally of the body 2.

Extending through the tube 9 from the support 8, through the fitting 11, and beyond, are at least two parallel optical fibers 14a and 14b. Externally of the probe the fibers 14 are enclosed in a flexible sheath 15. One of the fibers is coupled to a light source (not shown) and the other is coupled to one or more light detectors (not shown) for purposes to be explained in more detail hereinafter.

At the forward or inner end of the body extension 3 is a counterbore in which is accommodated a collimating lens 16. The lens has a plane surface which confronts the adjacent ends of the optical fibers 14 and a convex surface 17 which faces in the opposite direction.

The sleeve 4 has a skirt 18 which threadedly accommodates the extension 3. At the free end of the extension 3 is a sealing ring 19. A transparent, stepped window 20 has an enlarged diameter portion 21 abutting the sealing ring 19 and a reduced diameter portion 22 nesting with a flange 23 on the inner surface of the skirt 18. The window 20 has a first plane surface 24a confronting the lens 16 and a parallel, second plane surface 24b facing in the opposite direction. The surface 24a preferably abuts the lens 16.

Across the passage 6 from the window 20 the sleeve 4 terminates in an internally threaded end 25 in which is threadedly accommodated an annular retainer 26 having an inwardly extending, radial flange 27 at one end. Accommodated in the retainer is a reflector assembly 28 including a transparent, stepped disc 29 having a reduced diameter end 30 confronting the window 20. A protective backing disc 31 corresponding in size to the larger end of the disc 29 confronts the latter. Interposed between the confronting surfaces of the discs 29 and 31 is a coating 32 of aluminum or other suitable reflective material which preferably is applied to the entire surface area of the disc 29 by any conventional process. Following the application of the reflective material to the surface of the disc 29, the marginal edge of the coating is removed to form an annular groove 33 spaced from the outer surface of the coating 32 by the thickness of such coating. To the area of the groove is applied an adhesive, such as a suitable epoxy, which not only bonds the disc 29 to the disc 31, but also provides a seal peripherally of the coating 32 to protect the latter against damage from the fluid.

Also accommodated in the retainer 26 is a threaded plug 34 by means of which the reflective assembly 28 is maintained in snug engagement with the flange 27. A screwdriver slot 35 in the plug 34 facilitates rotation thereof.

A locking ring 36 is threaded onto the threaded exterior of the retainer 26 so as to abut the free end of the sleeve 4. A cap 37 also is threaded onto the retainer 26 to close the outer end thereof.

Fluid tight joints are provided between the several movable parts of the sleeve by convention seals (not shown) or such joints may be provided in any other known manner.

To condition the apparatus for operation the tube 9 is adjusted axially of and fixed in the body 2 at a distance sufficient to locate the coplanar inner ends of the optical fibers 14a, 14b at the focal length of the lens 16. The sleeve 4 is fitted onto the extension 3 and rotated to a position in which the window 20 abuts the seal 19. The retainer 26 may be adjusted to locate the reflector assembly 28 at a fixed distance from the window 20, thereby establishing a selected path length between the window and the reflector. The members 36 and 37 than may be secured in place on the extension 4 and that end of the probe containing the passage 6 immersed in a fluid.

One of the optical fibers (hereinafter sometimes referred to as the illuminating fiber 14a) is coupled to a suitable source of light and the other fiber (hereinafter sometimes referred to as the companion light collecting fiber 14b) is coupled to any suitable detector apparatus that is adapted to analyze in a known manner the wavelength, intensity, or any other selected characteristic of the reflected light emitted from such fiber.

Light discharged from the free end of the illuminating fiber 14a impinges on the plane surface of the lens 16 and is collimated so as to pass through the window 20 substantially perpendicularly to the surface 24a whence it traverses the space 6, passes through the transparent disc 29 and impinges at a small angle of incidence on the reflective surface 32. The reflective surface reflects the light back through the passage 6, through the window 20 and onto the surface 17 of the lens 16 from which it is focused onto the light collecting fiber 14b and transmitted thereby to the detector. The fibers 14 are so arranged as to be symmetrical about the longitudinal axes of the probe and the lens, thereby ensuring focusing of the reflected light onto the light collecting fiber.

By collimating the illuminating light so that it is substantially perpendicular to the surfaces of the window 20 and the reflector 28, there is little refraction of the light due to angular paths as it traverses the fluid medium. Thus, the transmission of light is not dependent on the refractive index of the fluid medium and, in the absence of absorbance by the medium, is affected very little by the path length. Further, the reflected light can be focused accurately onto the companion collecting fiber 14b.

The length of the light path from the window 20 to the reflective surface 32 is designated in FIG. 3 by the letter L. The length of the path L may be adjusted by rotation of the retainer 26 relative to the extension 3 so as to move the reflector assembly 28 as a unit toward or away from the window 20. Adjustment of the length of the light path enables the apparatus to be used with fluids of greatly differing translucency.

The distance between the illuminating and collecting fibers 14 and the lens 16 is designated by the letter F and corresponds to the focal length of the lens. This distance may be set when the parts of the probe are assembled. Since the tube 9 is adjustable relative to the body 2 and the fiber support 8 is adjustable relative to the tube 9, lenses of greatly different focal lengths may be used.

Although only one companion pair of optical fibers 14a, 14b is illustrated, two or more companion pairs may be used provided the light emitting fibers and the respective companion light collecting fibers are so arranged relative to the axes of the probe and the lens as to ensure that light from one light emitting fiber traverses the fluid medium and subsequently is reflected and focused only onto its companion light collecting fiber. Thus, such a probe may have independent optical paths which are coincident within the medium.

The probe 40 shown in FIGS. 5 and 6 comprises a body 41 having larger and smaller diameter sections 42 and 43 joined by a neck 44. At one end of the section 43 is a tubular extension 45 having a pair of diametrically opposed openings 46 therein forming a transverse passage 47 through which a fluid medium may flow. The free end of the extension 45 is internally threaded to accommodate a correspondingly threaded plug 48 having a screwdriver slot 49 at one end and a reduced end 50 in which is accommodated a reflector assembly 51 corresponding in all respects to the assembly 28. The plug 48 may be rotated to such position as to locate that end of the reflector assembly 51 which confronts the passage 47 in a selected position relative thereto.

The extension 45 has a smooth bore 52 at the opposite end of the passage 47 which forms a continuation of a smooth bore 53 formed in the body section 43. Slideably accommodated in the bores 52 and 53 is a sleeve 54 having a smooth outer surface and a threaded bore 55. That end of the sleeve 54 adjacent the passage 47 supports two plano-convex lenses 56 and 57, the convex surfaces confronting and abutting one another. The lenses are fixed and sealed in the sleeve 54 in the manner disclosed in connection with the lens 16, and the lens 57 functions as the window of the earlier embodiment.

Rotatably accommodated in the bore 55 of the sleeve 54 is an externally threaded optical fiber support 58 having at least two parallel passages 59 and 60 for the accommodation of a pair of optical fibers 61 and 62 having co-planar free ends, the free ends being flush with the right-hand or inner end of the support. The length of the support is such as to enable the inner end thereof to be located at the focal length of the lens 56 and the opposite end thereof to project beyond the corresponding end of the sleeve 54.

That end of the support 58 which projects beyond the sleeve 54 is threadedly received in the correspondingly threaded bore 63 at one end 64 of a tubular member 65 having circumferential grooves 66 for the accommodation of sealing 0 rings. Adjacent the grooves 66 is an enlarged section 67. The external surfaces of the sections 64 and 67 of the body 65 are smooth for slideable accommodation in the bores 52 and 53. The body section 67 terminates at its free end in an externally threaded extension 68 having a smooth bore 69 which communicates with the bore 63.

A differential nut 70 has an internally threaded bore 71 which threadedly accommodates the threaded extension 68. The nut 70 has an externally threaded surface 72 which is accommodated in the threaded end of the body section 42. A flange 73 is provided at one end of the nut 70 to facilitate rotation of the latter.

A companion pair of optical fibers 74 and 75 extend through the nut 70, the tubular member 65, and are fixed in the fiber support 58 with their adjacent ends flush with the inner end of the support. A flexible sheath (not shown) covers the fibers externally of the nut 70.

The pitch of the thread 71 corresponds to the pitch of the thread 68 and the pitch of the thread 72 corresponds to the pitch of the thread in the bore of the enlarged body portion 42. However, the pitches of the threads 71 and 72 do not correspond to one another. Instead, there is a differential between the pitches.

When the parts of the probe 40 are assembled in the manner shown in FIG. 5, rotation of the differential nut 70 in one direction will cause conjoint longitudinal movement of the assembled members 54, 58, and 65 so as to move the assembly of lenses 56 and 57 in a direction away from the mirror assembly 51, thereby increasing the length of the path between the lens 57 and the reflective surface of the reflector assembly 51. Conversely, rotation of the nut 70 in the opposite direction will cause the assembly of lenses to move in a direction toward the assembly 51, thereby shortening the length of the path between the lens and the reflective surface.

To ensure linear movement of the lenses and prevent inadvertent relative rotation of the several parts, a set screw 76 may be threaded into an elongate slot 77 formed in the section 42 of the body 41.

One of the advantageous characteristics of the probe 40 is that the length of the light path between the assembly of lenses and the reflector may be adjusted without having to remove the probe from the medium in which the passage 47 is immersed. The probe 40 also lends itself to adjustment of the length of the light path either manually or mechanically. That is, the nut 70 may be adjusted manually or the flange 73 of the nut may be coupled to a suitable, power driven mechanism to effect rotation of the nut.

The operating characteristics of the probe 40 correspond exactly to those described in connection with the probe 1.

We claim:

1. An improved light transmission probe comprising an elongate body having between its ends a transverse opening through which a fluid may pass; means for transmitting light from a source thereof across said opening along a path extending in a direction from one end of said opening toward the other; reflecting means spaced from said transmitting means for reflecting light impinging thereon across said opening in the opposite direction; collecting means for collecting said reflected light; and transparent collimating means interposed between said transmitting means and said reflecting means for collimating the transmitted light and focusing the reflected light onto said collecting means, wherein the improvement comprises: said reflecting means comprising a transparent member having a first surface facing said opening and a second surface remote from said opening; a protective member overlying said second surface; a light reflective coating interposed between said second surface and in engagement with said protective member, said light reflective coating having an area less than that of said second surface so that a marginal zone of uncoated second surface surrounds said light reflective coating; and adhesive means positioned in said marginal zone for securing said protective member to said second surface.

* * * * *